(12) United States Patent
Rabin et al.

(10) Patent No.: US 8,146,607 B2
(45) Date of Patent: Apr. 3, 2012

(54) VENTILATED DEVICE FOR DELIVERY OF AGENTS TO AND THROUGH THE HUMAN SCALP

(76) Inventors: Michael I. Rabin, Gates Mills, OH (US); David A. Smith, Gates Mills, OH (US)

( * ) Notice: Subject to any disclaimer, the term of this patent is extended or adjusted under 35 U.S.C. 154(b) by 454 days.

(21) Appl. No.: 12/182,815

(22) Filed: Jul. 30, 2008

(65) Prior Publication Data

US 2009/0032049 A1 Feb. 5, 2009

Related U.S. Application Data

(60) Provisional application No. 60/963,035, filed on Aug. 1, 2007.

(51) Int. Cl.
| | |
|---|---|
| *A45D 2/00* | (2006.01) |
| *A45D 7/04* | (2006.01) |
| *A45D 19/18* | (2006.01) |
| *A45D 44/08* | (2006.01) |
| *A61Q 5/00* | (2006.01) |
| *A42B 1/06* | (2006.01) |
| *A61M 35/00* | (2006.01) |
| *A61H 9/00* | (2006.01) |

(52) U.S. Cl. ............ 132/221; 4/521; 132/202; 132/207; 132/270; 2/410; 604/289; 601/159

(58) Field of Classification Search ....... 4/521; 47/21.1; 62/259.3; 132/270, 221, 228, 202, 274; 2/174, 2/171.2; 601/159, 15–17
See application file for complete search history.

(56) References Cited

U.S. PATENT DOCUMENTS

| | | | | |
|---|---|---|---|---|
| 998,803 | A | * | 7/1911 | Salisbury .......................... 4/518 |
| 998,804 | A | * | 7/1911 | Salisbury .......................... 4/518 |
| 1,772,501 | A | * | 8/1930 | Shelton .......................... 601/17 |
| 2,507,386 | A | | 5/1950 | Spiegel |
| 2,566,600 | A | * | 9/1951 | Colon .............................. 601/97 |
| 2,858,834 | A | | 11/1958 | Givens |
| 3,070,803 | A | * | 1/1963 | Slepicka .............................. 2/7 |
| 3,177,868 | A | * | 4/1965 | Wallace et al. ................ 601/159 |
| 4,078,557 | A | * | 3/1978 | Spencer ......................... 601/114 |
| 4,930,504 | A | | 6/1990 | Diamantopoulos et al. |

(Continued)

FOREIGN PATENT DOCUMENTS

EP 0130950 9/1985

OTHER PUBLICATIONS

T.I. Karu "Laser biostimulation: a photobiological phenomenon" (J. Photochemistry and Photobiology vol. B3, pp. 638-640 (1989)).

*Primary Examiner* — Tatyana Zalukaeva
*Assistant Examiner* — Susan Su
(74) *Attorney, Agent, or Firm* — K. David Crockett, Esq.; Paul J. Backofen, Esq.; Crockett & Crockett, PC

(57) ABSTRACT

A method and device for administering minoxidil and other topical solutions to the scalp. The method entails administering a minoxidil preparation through a manifold that fits over the scalp of a patient, and placing a moisture barrier over the scalp for a period of time effective to enhance absorption of the minoxidil preparation by the scalp.

6 Claims, 9 Drawing Sheets

U.S. PATENT DOCUMENTS

| | | | |
|---|---|---|---|
| 5,054,504 A * | 10/1991 | Winrow | 132/114 |
| 5,075,908 A * | 12/1991 | Newman | 4/521 |
| 5,616,140 A | 4/1997 | Prescott | |
| 5,755,752 A | 5/1998 | Segal | |
| 5,803,093 A | 9/1998 | Romano | |
| 5,951,596 A | 9/1999 | Bellinger | |
| 6,050,099 A * | 4/2000 | Lopa et al. | 62/259.3 |
| 6,050,990 A | 4/2000 | Tankovich et al. | |
| 6,210,381 B1 | 4/2001 | Morse | |
| 6,228,041 B1 * | 5/2001 | Ameer | 601/58 |
| 6,267,720 B1 | 7/2001 | Knox et al. | |
| 6,283,956 B1 | 9/2001 | McDaniel | |
| 6,588,964 B1 * | 7/2003 | Au et al. | 401/282 |
| 6,645,230 B2 | 11/2003 | Whitehurst | |
| 6,936,044 B2 | 8/2005 | McDaniel | |
| 7,530,961 B1 * | 5/2009 | Griffin | 601/49 |
| 2002/0071708 A1 * | 6/2002 | Fontanet et al. | 401/202 |
| 2002/0111591 A1 | 8/2002 | McKinnon et al. | |
| 2004/0097890 A1 | 5/2004 | Wilkinson | |
| 2004/0153131 A1 | 8/2004 | Yorke | |
| 2005/0283110 A1 * | 12/2005 | Atala et al. | 604/20 |
| 2006/0178713 A1 | 8/2006 | Maricle et al. | |

* cited by examiner

Fig. 7
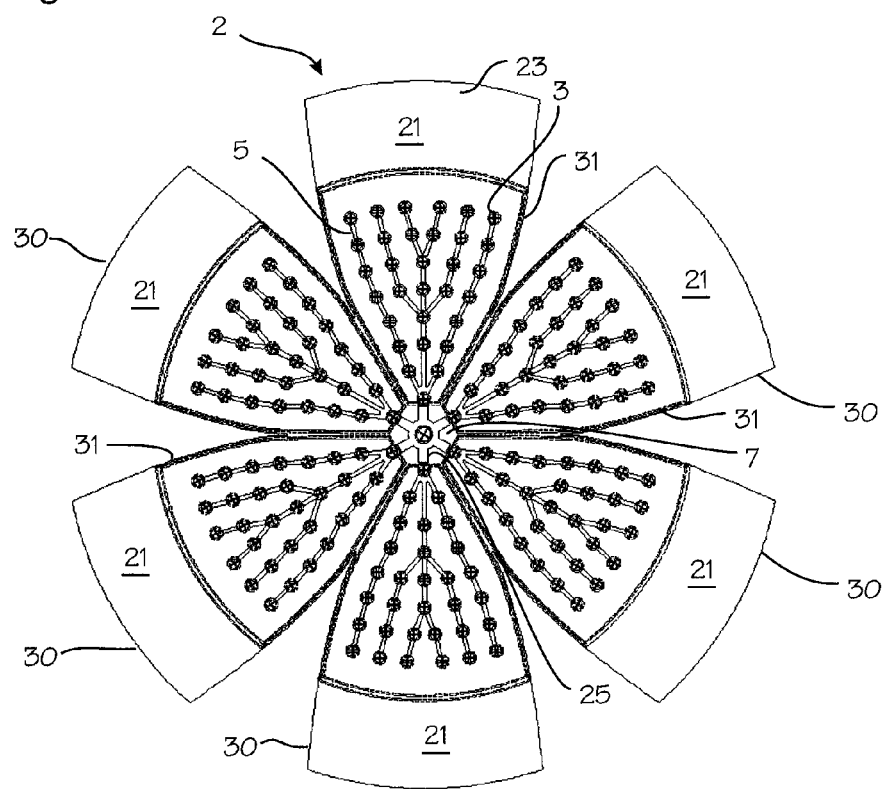
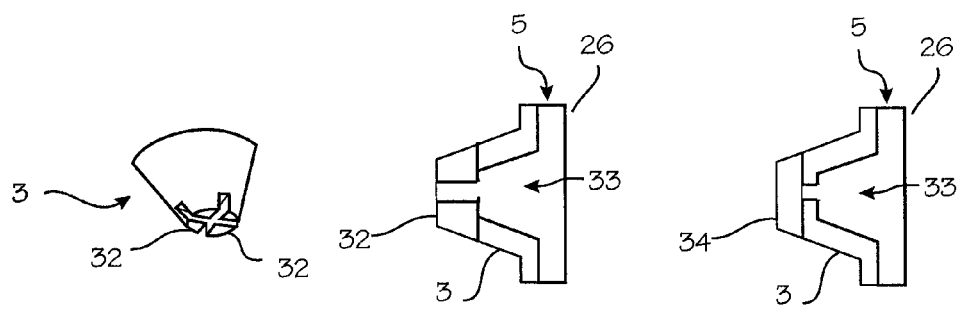
Fig. 8  Fig. 8a  Fig. 9

VENTILATED DEVICE FOR DELIVERY OF AGENTS TO AND THROUGH THE HUMAN SCALP

RELATED APPLICATIONS

This application claims priority from U.S. Provisional patent application 60/963,035 filed Aug. 1, 2007.

FIELD OF THE INVENTIONS

The inventions described below relate to the field of hair regrowth and treatments for baldness.

BACKGROUND OF THE INVENTIONS

Minoxidil has proven to be an effective treatment for baldness. Specifically, it can stop and reverse ongoing hair loss and stimulate hair growth in adult men and women who are losing hair due to male or female pattern baldness (androgenic alopecia). However, minoxidil is only effective if properly applied. Minoxidil is applied with an eye-dropper, followed by careful massage of the applied solution to distribute it over the scalp. This is a tedious process, given that the typical user must apply minoxidil through the hair, and avoid wasting the minoxidil by wetting the hair instead of the scalp. Minoxidil must be applied twice daily for effective treatment. The desired result of renewed hair growth is obtained after several weeks or months of use. The twice-daily regimen must be continued indefinitely to maintain the effect, and if discontinued, any hair re-grown will be lost.

Due to the tedious nature of the regimen, most patients do not comply with the regimen. Because they do not maintain the regimen, the drug does not work, and patients discontinue the regimen, thereby abandoning an otherwise beneficial treatment.

SUMMARY

The devices and methods described below provide for a more convenient application of minoxidil, other suitable chemicals or other treatment to the scalp, to enhance patient compliance and/or permit a less rigorous treatment regimen. The device comprises a hat with a distribution manifold adapted to distribute minoxidil about the scalp, an injection port for injecting minoxidil into the manifold, and a reservoir for taking up a dose of minoxidil and injecting it into the manifold. The manifold includes numerous outlet nozzles that protrude, when the cap is in place, from the interior of the hat toward the scalp of the patient, and preferably contact the scalp. The hat is used by the patient by injecting a minoxidil solution into the manifold and hence through the nozzles onto the scalp, and thereafter wearing the hat for a period of time suitable to promote absorption of the distributed minoxidil.

An alternative treatment apparatus includes a disposable lattice hat liner that may operate as a distribution manifold for liquid or foam scalp or hair restoration treatments. The disposable lattice may also operate as an electrical distribution buss to support any suitable light therapy. Some portion of the lattice intersections may include inactive bristles as spacers to support the lattice at a fixed distance from the users scalp. Active bristles may permit active or passive dispensing of treatment compounds where passive dispensing relies on proximity of the passive bristle to the user's scalp and or temperature, pressure or other trigger to convey treatment compound to the user's scalp.

An alternate treatment lattice may also include vibration or ultrasound transmitted through the lattice to enhance treatment efficacy. Vibration and or ultrasound may also be combined with treatment compounds and or phototherapy.

BRIEF DESCRIPTION OF THE DRAWINGS

FIG. 7 is a bottom view of the manifold of FIG. 6.

FIGS. 8, 8a and 9 illustrate nozzle constructions for use in the device.

DETAILED DESCRIPTION OF THE INVENTIONS

Figure 1:
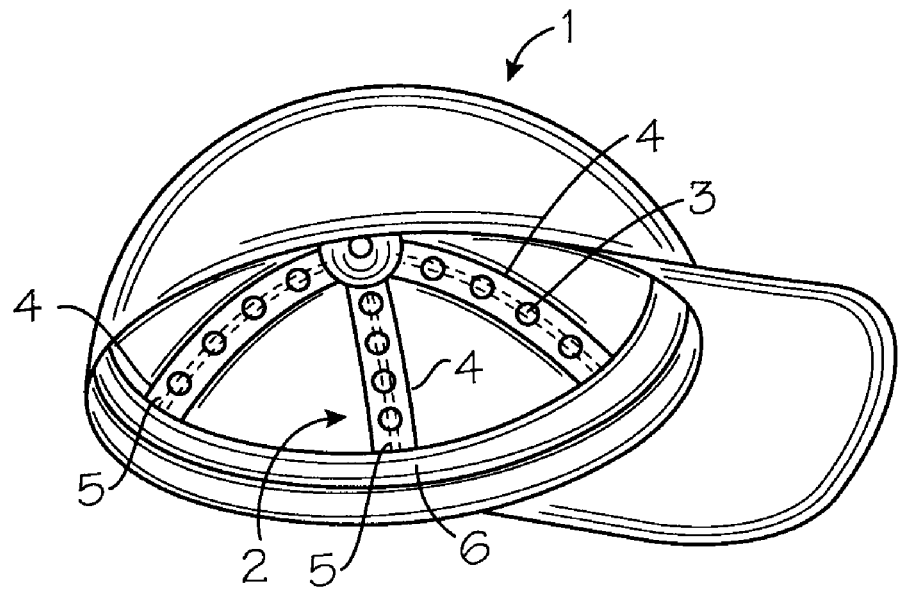
FIG. 1 is a bottom perspective view of the cap to be used for distribution of minoxidil to the scalp of a patient.

FIG. 1 is a bottom view of cap 1 to be used for distribution of hair-regrowth topical solutions, such as minoxidil preparations, to the scalp of a patient. The cap covers a manifold 2 supporting an array of nozzles 3 distributed about the inner surface of the hat. The manifold comprises several arms 4 with lumens 5 communicating with the nozzles. The manifold arms may be embedded in, or covered by, a neoprene liner which fits within the cap. An occlusive band 6 is disposed about the perimeter of the cap, on the interior surface. The occlusive band may be elastic and tight-fitting to provide a tight-fitting sealing gasket between the user's scalp and the cap, or may be somewhat loose and merely promote creation of a closed environment of relatively high humidity immediately proximate the scalp.

Figure 2:
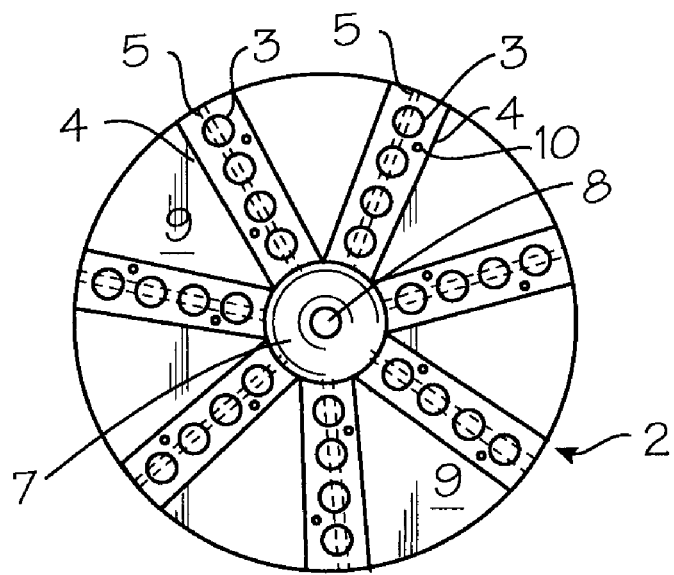
FIG. 2 is a bottom view of a manifold used with the cap of FIG. 1.

The manifold 2 is shown more clearly in FIG. 2, in which the manifold and the several arms are shown. The lumens 5 (shown in phantom) extend from the plenum or distribution chamber 7 in the center of the manifold, and are in fluid communication with the valved fitting 8 and the several nozzles providing outlet ports from the lumen. The manifold may be embedded in or covered with material 9 such as neoprene, cloth, polyurethane or other suitable material, such that any tubing establishing the lumens, or manifold arms, are conveniently held in the desired array. This material, or the material of the cap, is provided in sufficient density to serve as a moisture barrier to enclose the environment immediately about the hair and/or scalp while in use.

The nozzles 3 are arranged on the interior surface of the cap so that, when the cap is worn, the nozzles will be disposed proximate the appropriate treatment target zones on the scalp, such as the vertex, occiput (back of the head), and frontal areas, and project toward the scalp from the interior surface of the manifold. Additional projections 10 can be provided on the interior surface of the cap. Both the nozzles and the additional projections can be formed in various sizes and profiles, such as blunt flat distal faces or sharp or abrasive distal surfaces, to aid in distribution of the applied minoxidil, or to provide complimentary treatment such as micro-abrasion. Some of the projections may be taller than nearby nozzles to maintain a small gap between the nozzles and the scalp. The manifold and manifold arms are sized and dimensioned, and positioned within the cap, so that they lie over the desired portions of the scalp (vertex, occiput, and frontal areas) when the cap is worn in typical fashion (bill forward, hat band level on the head). The lumens of the manifold are sized to permit slow drainage of the minoxidil preparation, which may be watery or slightly viscous, and the lumens may be varied in size to suit the actual viscosity of the preparation used (commercially available minoxidil preparations such as Rogaine® have low viscosity, like water, though they are mixture of ethanol and slightly viscous propylene glycol).

Figure 3:
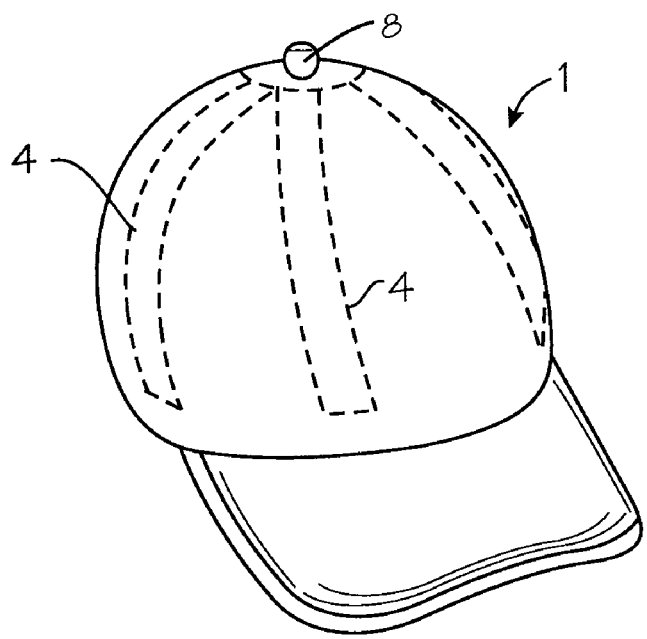
FIG. 3 is a side view of cap to be used for distribution of minoxidil to the scalp of a patient.

FIG. 3 is a side view of the cap of FIG. 1. An inlet port in form of a valved fitting 8 is disposed on the exterior of the cap, and provides a fluid pathway for injecting minoxidil into the manifold. The fitting is adapted to receive a minoxidil preparation from a source such as a pressurized can or bellows reservoir. The fitting is in fluid communication with lumens of the manifold, and is disposed in the central plenum connecting the various manifold arms. The baseball cap provides positioning support for the manifold and nozzle array, positioning support for the seal, and ornamental disguise for the manifold. The baseball cap may be replaced by any style of hat, or altogether omitted if the occlusive band 6 (or other head band) is secured to the manifold, or if the moisture barrier is sufficiently sturdy to maintain the form of manifold (either or both may be used in combination without the cap). Any style of cap may provide the desired support and positioning means for the manifold and nozzle array, and any style of cap, hat, headband or hood can be used as the means of disguise. Also, the manifold may be used without the cap, moisture barrier or occlusive band to distribute the preparation.

Figure 4:
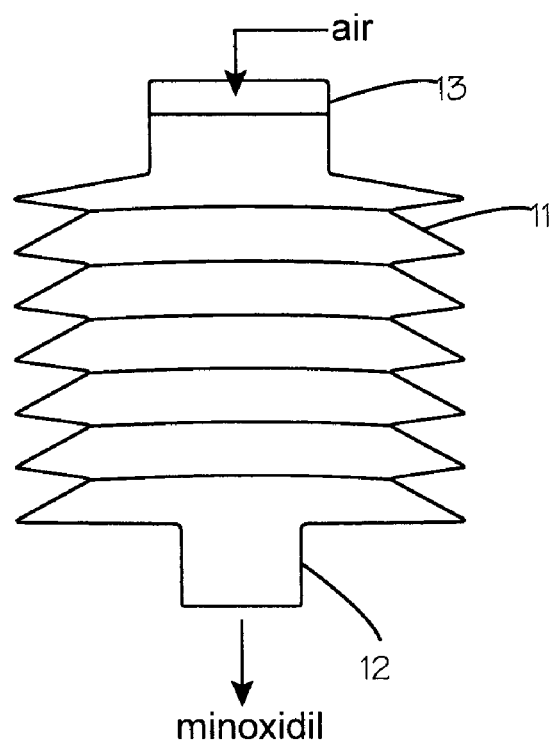
FIG. 4 illustrates a reservoir for use with the cap.

A suitable reservoir 11, shown in FIG. 4 is sized to hold a single dose of minoxidil preparation. This reservoir is a bladder or bellows pump, with an outlet 12 adapted to provide a sealed connection with the cap fitting 8 and an inlet check valve 13 to take in air that can subsequently be pumped into the manifold to force the entire dose of minoxidil through the manifold and onto the scalp. The bellows may be sized to accommodate a single dose of preparation, and may be provided as a disposable or re-usable form. As an alternative, a typical bladder pump of the type used to inflate bladders in clothing can be installed in the cap, and the minoxidil preparation can be supplied in single dose capsules that can be fitted to the intake of the bladder pump such that operation of the pump first empties the bladder into the manifold and then pumps air or other fluid suitable for clearing the manifold into the manifold to clear the manifold. Any other pump means may be used, including simple syringes, squeeze bottles, tubes, etc., with appropriate connectors for connection to the cap, in place of the bladder pump.

Figure 5:
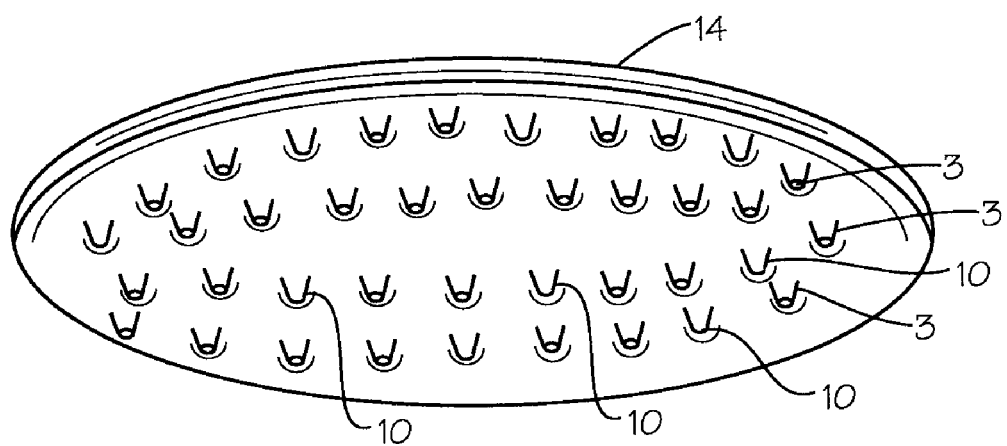
FIG. 5 illustrates an alternative embodiment of the manifold.

FIG. 5 illustrates an alternative embodiment of the manifold, which includes a brush-like body 14 with numerous nozzles 3 and projections 10 depending downwardly (or toward the scalp) from the body toward the scalp when positioned, along with the cap, on the user's head. When fitted within the cap, the manifold is bowl-shaped. The brush like body is sized and dimensioned, and positioned within the cap, so that it lies over the vertex of the head when the cap is worn in typical fashion (bill forward, hat band level on the head).

Figure 6:
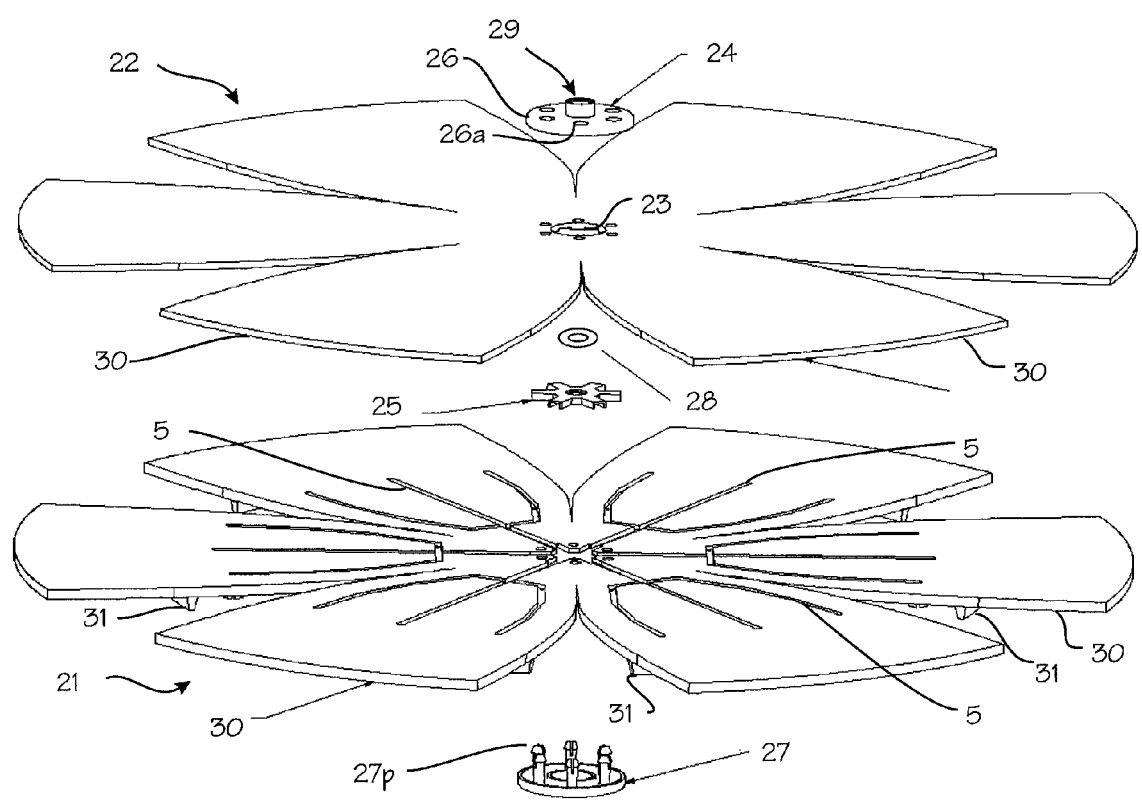
FIG. 6 illustrates a manifold that is constructed from two molded pieces.

FIGS. 6 and 7 illustrate a manifold that is constructed from two molded pieces. The manifold 2 comprises a molded lower sheet 21 in which the lumens 5 of the manifold are molded into the interior surface and the nozzles 3 are molded into the this sheet. The upper sheet 22 roughly matches the shape of the lower sheet, and is sealed to the bottom sheet so as to fully define the various lumens. The upper sheet includes the aperture 23 for passage of a connector 24 and connection between the connector and the channel distribution manifold 25. The connector includes a flange 26 various apertures 26a in the flange. This flange is arranged to match the multi-post detent ring 27 such that the apertures may receive the detent posts 27p on the detent ring when forced together to trap the channel distribution manifold 25, o-ring 28, and the upper and lower sheets of the manifold 2 together so that the fluid pathway through the connector lumen 29 and channel distribution manifold into the lumens 5 is established. The manifold upper and lower sheets are molded to form a flat sheet, with several gores (generally triangular sections) 30, which can be joined along their respective edges to create the convex cap to fit over the head of the user and within a cap or hat.

FIG. 7 is a bottom view of the manifold of FIG. 6 showing the surface of lower sheet 21. The numerous nozzles 3 extend from the inner layer, and overlie the underlying lumens 5 to provide fluid outlets for any preparation within the lumens. The lumens channel fluid from the distribution chamber 7 and/or channel distribution manifold 25 to the individual nozzles. The gores 30 may include slightly raised borders 31 which, when the gores are joined at their adjacent edges to form the convex cap, provide a degree of isolation and damming for each section.

FIGS. 8, 8a and 9 illustrate nozzle constructions for use in the device. In FIGS. 8 and 8a, the nozzle 3 includes several posts 32 extending distally from the distal aperture of the nozzle lumen 33, to provide some stand-off structure to hold the nozzle outlet away from the scalp and thereby prevent blockage of the nozzle aperture. The nozzle shown in FIG. 9 includes a foam or sponge tip 34 surrounding or covering the nozzle lumen 33. The foam tip may be useful in slowing the leakage or ejection of some preparations from the manifold, and hold preparation in contact with the user's scalp.

Figure 10:
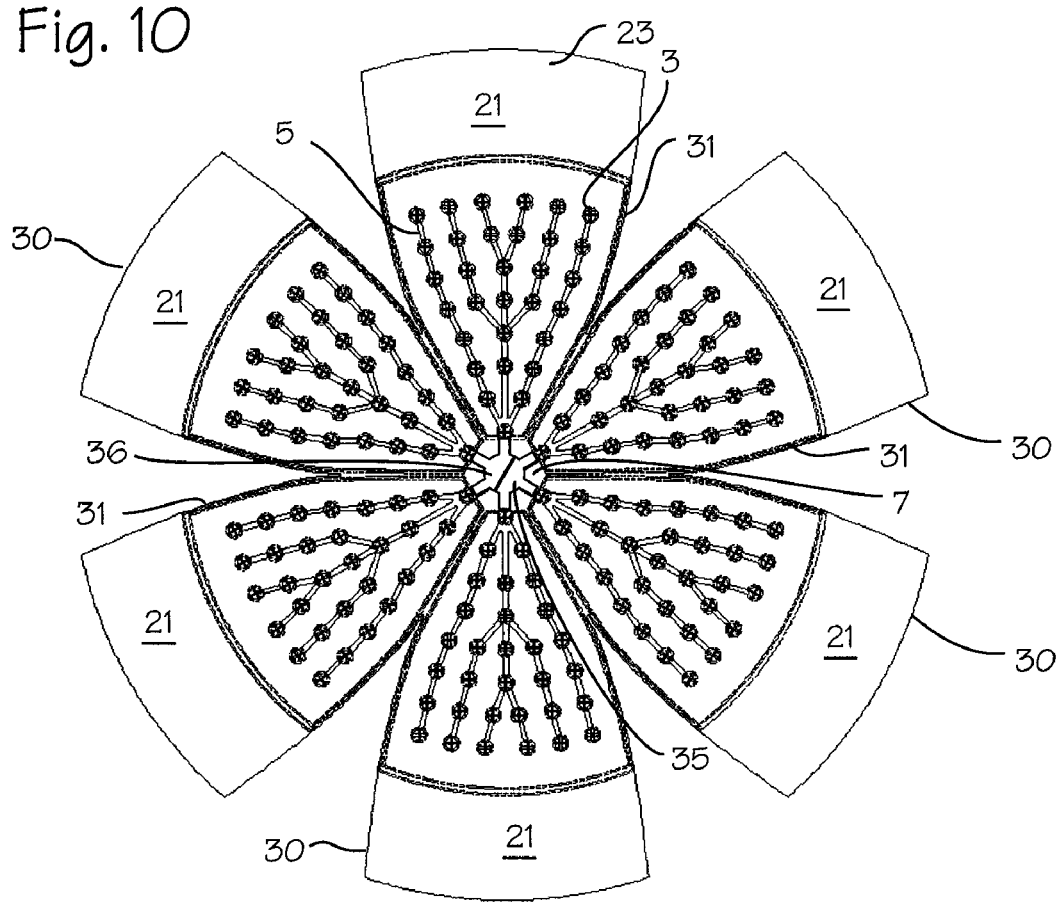
FIG. 10 illustrates a manifold suitable for application of different solutions on different areas of the patient's head.

FIG. 10 illustrates a manifold suitable for application of different solutions on different areas of the patient's head. This construction facilitates testing of the device, such that the experimental control required for rigorous analysis may be provided on each patient by applying therapeutically active preparation in one areas and an inactive placebo preparation in another area. The manifold is split, either side-to-side or front-to-back, in two isolated sides, separating the distribution chamber or distribution manifold into two isolated chambers, with each chamber aligned to several of the lumens. First and second inlets 35 and 36 may be used to supply solutions to each side of the manifold. Various means may be used to facilitate an experimental protocol in which users apply therapeutically active preparation to one side of the manifold and an inactive placebo preparation the other side of the manifold. For example, single doses of active preparation and placebo can be provided in bellows pump or other single dose reservoirs which have outlet connectors keyed to the inlet connectors of the manifold, such that the physical shape of each reservoir fits only on one manifold inlet or the other. Users engaged in the experimental protocol can then be provided with single dose reservoirs of active preparation that can be fitted only to one side of the manifold, and single dose reservoirs of placebo preparation that can be fitted only to the other side of the manifold. The bladder pump reservoir may be divided into two chambers as well, with one chamber filled with therapeutically active preparation in one chamber and an inactive placebo preparation in the other chamber, and be provided with a dual lumen connector which is keyed to the inlet such that it must be connected to the manifold connector to supply active preparation to one side and placebo to the other.

Figure 11:
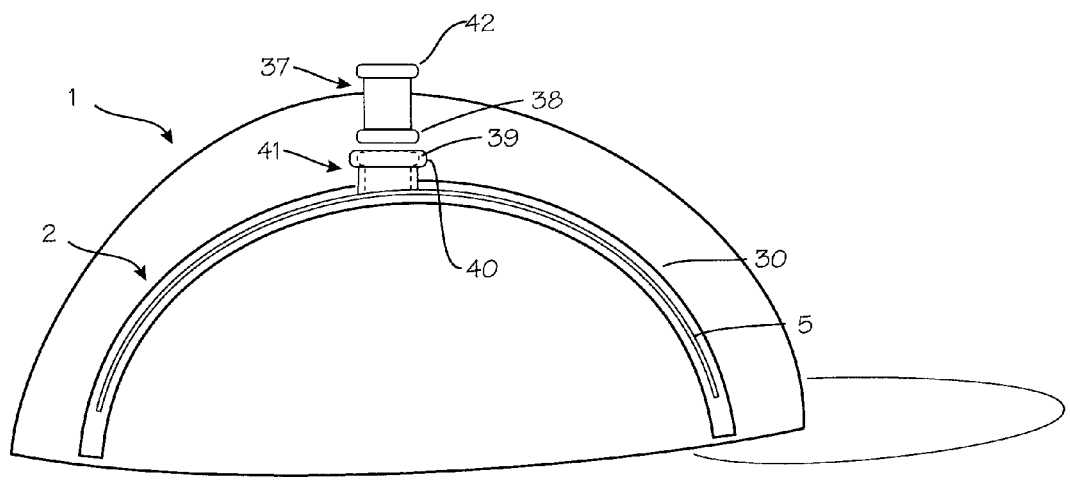
FIG. 11 illustrates a combination of cap and manifold that permits re-use of the cap with disposable manifolds.
Figure 12:
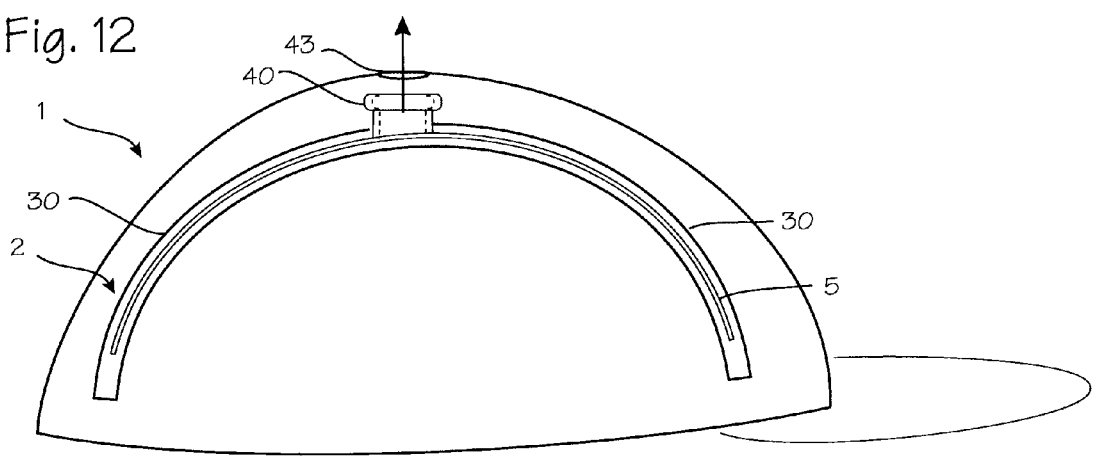
FIG. 12 illustrates a combination of cap and manifold that permits re-use of the cap with disposable manifolds.

FIG. 11 illustrates a combination of cap 1 and manifold 2 that permits re-use of the cap with disposable manifolds. The baseball cap is provided with a connector tube 37 in lieu of the traditional rivet and snap. This connector tube includes fixation and sealing structures adapted to connect to the manifold inlet and to the pump bottle, so that the manifold may be releasably yet securely fixed to the connector, used for a period of time, and removed and discarded when it becomes dirty. The internal fixation and sealing structure comprises a protruding ridge or bead 38 on the connector tube, which serves as a snap-lock bead which engages the matching groove 39 on the inside of snap-lock ring 40 of the manifold inlet port 41. The external fixation and sealing structure for connection to the pump may similarly comprise a similar protruding ridge or bead 42, or may be any other suitable connector that provides the moderate sealing capability required for transfer of the preparation from the pump to the connector without excessive leakage. The connector may be formed integrally with a typical rivet and snap assembly used in baseball caps. As an alternative, the baseball cap can be constructed with an aperture at the crown, and the connector tube may be fixed to the manifold above the manifold inlet, as shown in FIG. 12. The connector in this embodiment is sized to fit through the cap aperture 43, and may be provided with snap-lock beads or a button flange (a flange around the tube that is operable like a button with the crown aperture of the cap). These and various other means for releasably securing the manifold to the cap, such that it may be removed without use of tools and without the need to deconstruct the cap, may be used to facilitate re-use the ornamental cap with numerous manifolds.

To use the cap, a user wears the cap in regular sessions, according to the appropriate treatment regimen, applying the minoxidil preparation through the cap for each session. Twice daily sessions, in which the cap is worn for about an hour, are adequate to provide effective treatment in lieu of the twice-daily eye-dropper application. A 1 cc volume of standard commercially available minoxidil preparation, or other amount effective to promote hair growth in other formulations, may be used. The injection of minoxidil may be accomplished before or after the user dons the cap, but the flushing of air or other fluid to clear the manifold should be done when the cap is in place. While wearing the cap, the user may engage in any activity, preferably for about 10 to 60 minutes, and more preferably for about 15 minutes. The user thereby holds the vapor barrier over the scalp for a period after application effective to enhance absorption of the minoxidil preparation by the scalp. After each session, the user may wash and style his hair as usual.

To use the device with the disposable manifold shown in FIGS. 11 and 12, the user may snap the manifold inlet port 41 over the connector tube 37 (referring to FIG. 11), or slip the connector tube and its snap-ring through the cap aperture, button-like, to secure the manifold to the cap, and use the device as described above. When and if the manifold is worn out or dirty, the user then removes the manifold and installs a new manifold, so that the cosmetic cap can be used with a series of manifolds.

The device and method may be used to for hair re-growth using minoxidil or other hear re-growth compounds to re-grow hair, or prophylactically to prevent hair loss, or both. While minoxidil is generally referred to as a hair regrowth preparation, it also functions as a prophylactic hair maintenance preparation. Other compounds that perform solely as prophylactic hair maintenance preparations may be used in the method.

As mentioned above, the reservoir may be provided as a single dose reservoir, in either disposable or re-usable form. The re-usable reservoir is used by first connecting the suction end of the bellows/bladder pump to a larger reservoir of minoxidil preparation and operating the pump to fill the reservoir, and thereafter connecting the outlet end of the pump to the inlet port of the cap and operating the pump to pump the minoxidil preparation into the manifold, and then pump air or other flushing agent into the manifold to flush any minoxidil preparation in the manifold onto the scalp.

The device may be augmented with features that assist in the penetration or retention of the hair regrowth preparation, or augment the hair re-growth by other mechanisms. As mentioned above, the nozzles and projections may be modified with the addition of abrasive surfaces, bristles, or sharp, needle-like projections to provide for micro-abrasion of the scalp that is accomplished by the normal movements of the cap during use. The nozzles may be tipped with sponge or other absorbent material to aid in distribution of the preparation. For patients that are bald, either by choice or advanced hair loss, the manifold may be covered, over its interior surfaces, by a sheet of sponge, felt or other diffusive material. Also for patients with short hair or no hair, the nozzles may be very short, or omitted altogether, so that ports on the interior of the manifold open directly onto the scalp. The devices may be augmented with the addition of LED's or other light sources to provide illumination in the interior of the cap, to irradiate the scalp with appropriate visible light wavelengths, as taught by Yorke, Apparatus And Method For Hair Retention And Regeneration, U.S. Pub. 2004/0153131 (Aug. 5, 2005), or with other suitable wavelengths.

Figure 13:
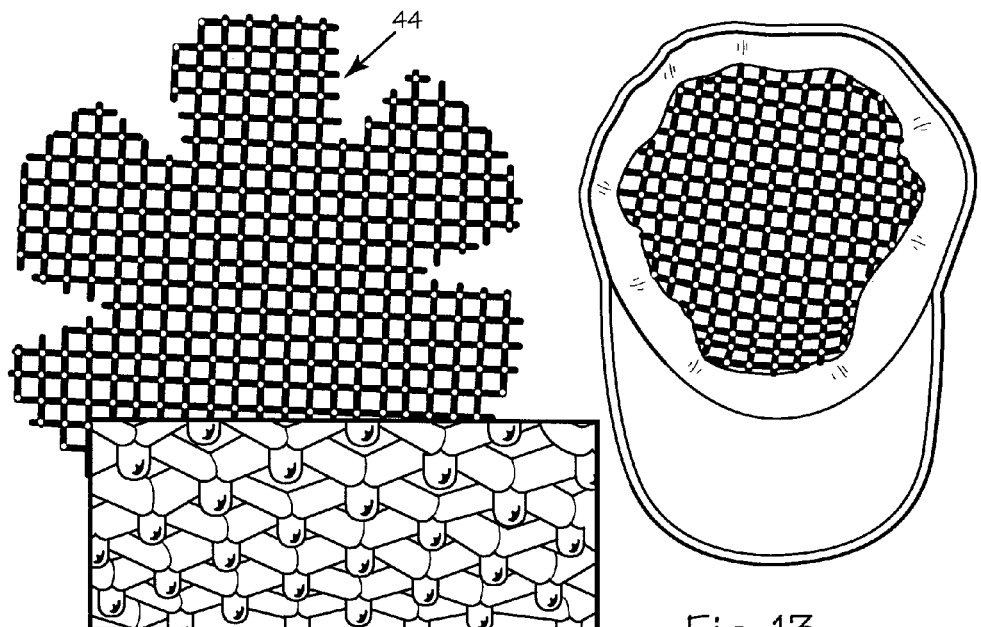
FIG. 13 is an illustration of a disposable lattice prototype with a close-up view of the bristles.
Figure 14:
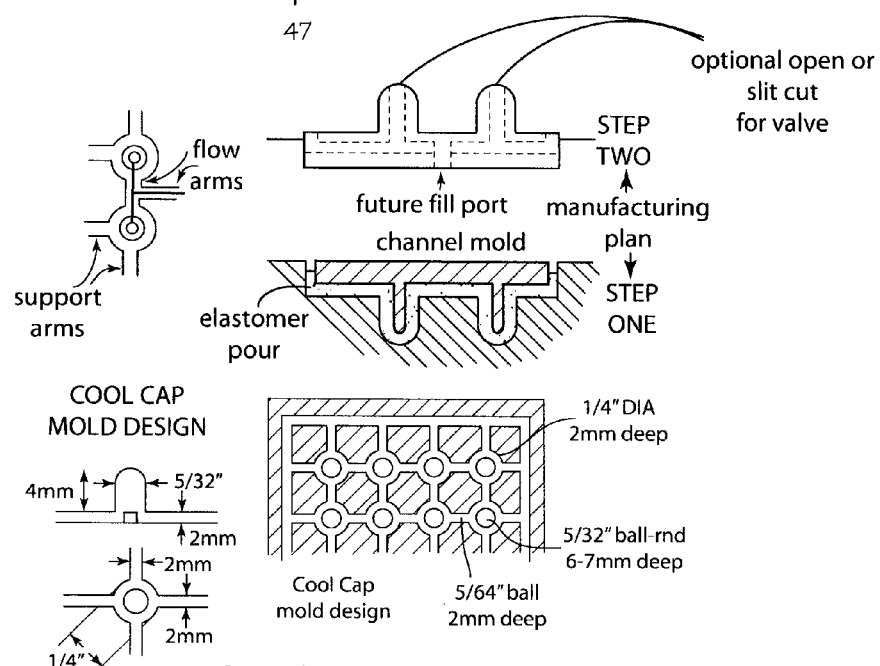
FIG. 14 is an illustration of alternative configurations for fluid delivery bristles.
Figure 15:
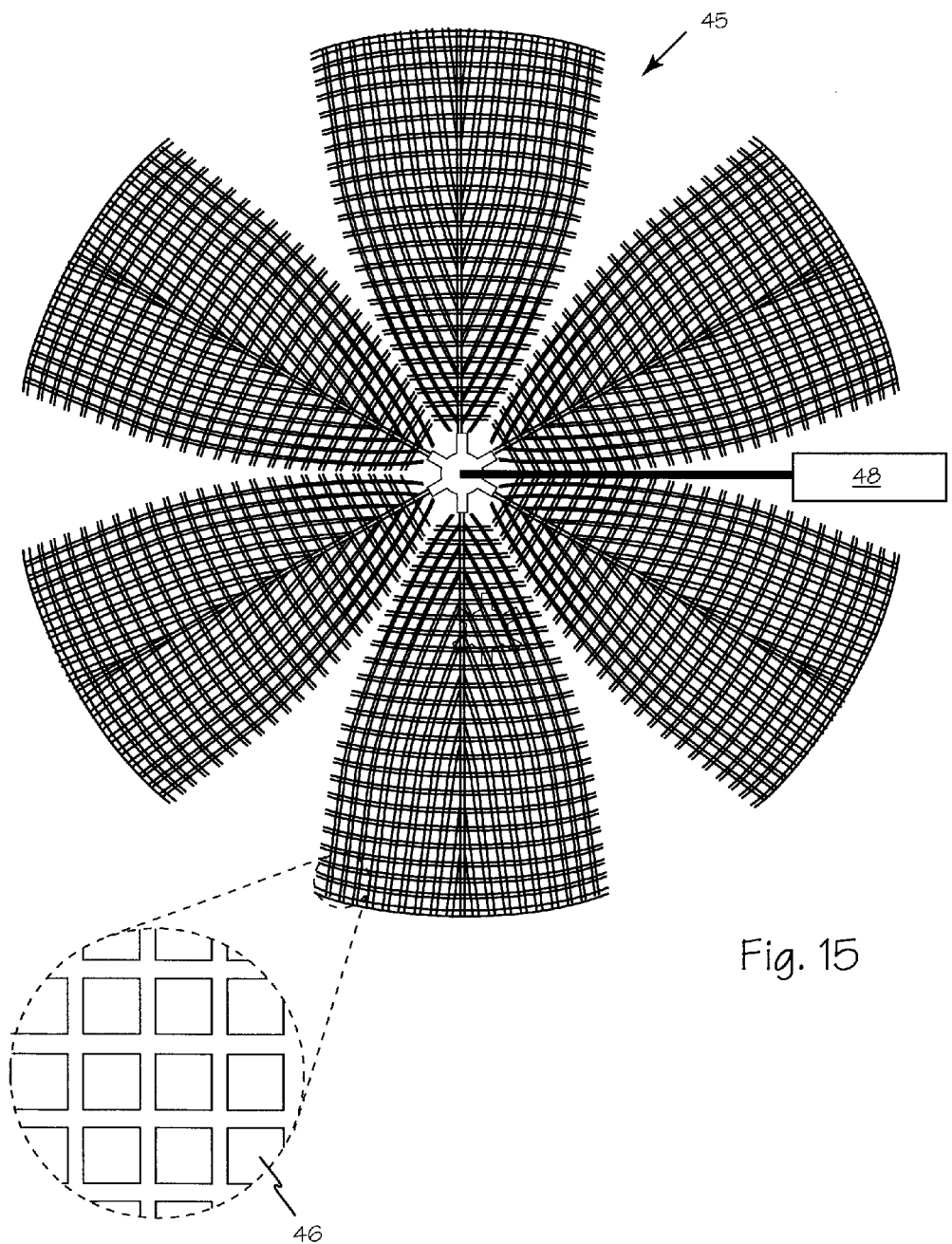
FIG. 15 is a top view of a disposable lattice liner formed in a six-wing configuration.

To improve ventilation near the user's scalp, a treatment manifold may be formed as a lattice such as lattice 44 as shown in FIG. 13 and or lattice 45 of FIG. 15. Openings such as opening 46 eliminate material from the lattice manifold lowering the weight and providing ventilation ports. Nozzles or bristles such as bristle 47 also provide an offset from the user's scalp promoting air circulation between the scalp and the lattice and reduce the likelihood of compression of the hair beneath the lattice.

In an active lattice configuration, all or a portion of a lattice such as lattice 44 and or lattice 45 may be driven by any suitable vibration source such as motor 48 to motivate the bristles to provide therapeutic massage to the scalp. The use of ultrasonic or other suitable vibration may employ the bristles to accomplish microderm abrasion. The lattice may also support phototherapy light sources such as LEDs or other suitable lights which may be used together or separately from the active vibration and or the application of hair restoration compounds.

The devices and methods described above have been described in relationship to the application of minoxidil, which is the currently predominant hair re-growth preparation available today. Nonetheless, the devices and methods may be employed with any other hair re-growth compound or preparation, any hair loss prophylactic preparation, and with other cosmetic and/or therapeutic agents such as topical finasteride, minoxidil, ketoconazole, steroids, other anti-microbials, steroids, copper peptides for post-hair transplantation wound healing, anti-androgens, antimicrobials, spironolactone, spironolactone-like compounds, progesterone derivatives, betametazone valerate, ketoconazole, zinc salts, Zinc Pyrithione ZnP, finasteride, flutamide, dutasteride, melatonin, photo-activated compounds, lice treatments, cosmetic preparations such as scalp dye, hair dye, hair gel, conditioner, moisturizer, scalp oils, hair "volumizers," vitamins, minerals, herbals, therapeutic water, zinc, iron, biotin, folic acid, anti-androgens, tretinoin, azelaic acid, and saw palmetto. The preparations may be provided in liquids of various viscosity, or in foams or other fluids, slurries or suspensions. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:
1. A device comprising:
an open lattice manifold sized and dimensioned to cover a portion of the scalp, said lattice manifold having a interior surface adapted to appose the scalp and an outer surface, and a fluid inlet port;
a plurality of nozzles depending from the interior surface of the lattice manifold, each of the plurality of nozzles having a foam tip adapted for contact with the scalp;
a reservoir of hair regrowth topical solution in fluid communication with the lattice manifold for conducting the hair regrowth topical solution through the lattice manifold and the plurality of nozzles to the scalp of a user; and
a moisture barrier disposed about the lattice manifold, said moisture barrier sized to cover a portion of the scalp;
said lattice manifold and moisture barrier shaped to fit over the scalp of the user.
2. The device of claim 1 further comprising:
one or more ultrasonic vibration sources engaging one or more portions of the lattice manifold to provide ultrasonic vibration therapy.
3. The device of claim 1 further comprising:
an ornamental cap for housing the lattice manifold, and moisture barrier, wherein the manifold is secured to the inside of the cap and the fluid inlet port protrudes from the inside of the cap to the exterior of the cap.
4. The device of claim 3, wherein the inlet port protrudes from the crown of the cap.
5. The device of claim 4, wherein the cap comprises a baseball cap, and the inlet port protrudes from the crown of the cap.
6. A method of treating hair loss comprising:
providing the device of claim 1;
placing the open lattice manifold over the scalp of the patient and injecting the hair-regrowth topical solution onto the scalp through the manifold and nozzles to apply the hair-regrowth topical solution to the scalp of the patient.

* * * * *